(12) United States Patent
Yonehama et al.

(10) Patent No.: US 6,562,934 B2
(45) Date of Patent: May 13, 2003

(54) AMINO COMPOUND AND PROCESS FOR PRODUCING THE SAME

(75) Inventors: Shinichi Yonehama, Hiratsuka (JP); Tetsushi Ichikawa, Hiratsuka (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/948,954

(22) Filed: Sep. 10, 2001

(65) Prior Publication Data

US 2002/0055605 A1 May 9, 2002

(30) Foreign Application Priority Data

Sep. 12, 2000 (JP) .......................................... 2000-276308

(51) Int. Cl.⁷ ............................................... C08G 59/50
(52) U.S. Cl. ........................ 528/122; 528/407; 528/418; 528/422; 564/336; 564/373; 564/388; 564/408; 564/462
(58) Field of Search ........................... 523/457; 528/122, 528/407, 418, 421; 564/336, 373, 388, 408, 462

(56) References Cited

U.S. PATENT DOCUMENTS 4,034,040 A * 7/1977 Cronin

FOREIGN PATENT DOCUMENTS

| JP | 55-11523 | 1/1980 |
| JP | 8-269196 | 10/1996 |
| JP | 11-80322 | 3/1999 |

* cited by examiner

Primary Examiner—Robert Dawson
Assistant Examiner—D. Aylward
(74) Attorney, Agent, or Firm—Armstrong, Westerman & Hattori, LLP

(57) ABSTRACT

An amino compound obtained by addition reaction of diamine represented by the following formula (1) and an alkenyl compound and a process for producing the same.

$$H_2N—H_2C—A—CH_2—NH_2 \qquad (1)$$

wherein A is a phenylene group or a cyclohexylene group.

10 Claims, 2 Drawing Sheets

US 6,562,934 B2

AMINO COMPOUND AND PROCESS FOR PRODUCING THE SAME

BACKGROUND OF THE INVENTION

1) Field of the Invention

The present invention relates to an amino compound obtained by addition reaction of an alkenyl compound to a diamine represented by the following formula (1) and a process for producing the same. This amino compound is applicable to a curing agent and a raw material thereof for an epoxy resin to be utilized in a very wide field including application to coating such as an electrodeposition coating for motor car, a heavy-duty paint for ship, bridge and land and marine iron structure, and inner coat of drinking can, application to electricity and electronics to be used in household electric products, communication equipments and control systems of motor car and airplane such as a laminated plate, an electric semiconductor sealing compound, an insulating powder coating, and coil impregnation, application to civil engineering and construction such as earthquake-proof of bridge, lining, reinforcement and repair of concrete structure, a flooring material of building, lining of water supplying facility and sewerage, and pavement for waste water and permeating water, application to adhesive for vehicle and airplane, and application to composite material for airplane, industrial materials and sports equipment, and to a chain extender and a raw material thereof of a polyurethane resin to be utilized in a very wide field including cloths, sports equipment, home appliances, electronics, medical apparatuses, motor cars, transporting apparatus, civil engineering and construction and industrial materials as foam, elastomer, coating, adhesive, binder, fiber, leather, flooring material, water proof material, athletic material, sealant, coking, medical material and fiber treating agent.

$$H_2N-H_2C-A-CH_2-NH_2 \tag{1}$$

wherein A is a phenylene group or a cyclohexylene group.

2) Prior Art

It has widely known that various polyamino compounds are used as a curing agent for epoxy resin and a raw material thereof or a chain extender and a raw material thereof of a polyurethane resin. Particularly, a curing agent for epoxy resin containing the diamine represented by the formula (1) and a curing agent for epoxy resin used the above-mentioned diamine as a raw material have a feature that curing of an epoxy resin composition fast proceeds since their reactivity with an epoxy resin is higher than a curing agent for epoxy resin containing other aromatic polyamino compound or an aliphatic polyamino compound and a curing agent for epoxy resin used the same as a raw material. Further they have features to provide a coated film excellent in both gloss and levelling and a cured product excellent in both water resistance and chemical resistance.

However, on the other hand, a curing agent for epoxy resin containing the diamine represented by the formula (1) and a curing agent for epoxy resin used the above-mentioned diamine as a raw material have defects that an epoxy resin composition used said curing agent for epoxy resin exhibits a short pot life and its workability is inferior since their reactivity with an epoxy resin is high.

Hitherto, it has been known that when a cyanoethylated polyamino compound obtainable by Michael addition reaction of a polyamino compound and an acrylonitrile is used as a curing agent for epoxy resin, long pot life is provided to an epoxy resin composition, e.g., "New Epoxy Resin" edited by Hiroshi Kakiuchi, published by Shokodo in Japan, 1985, P186. However, acrylonitrile has been designated as a specific chemical substance and a deleterious substance in Japan and exhibits high harmfulness. Thus, recently, restriction on its handling has been increased from the aspects of safety and hygiene.

Further, Japanese Patent Kokai (Laid-open) No. 8-269196 relates to a process for producing a star form-or a comb form-branched aliphatic polyamino compound and a curing resin composition and discloses an aliphatic polyamino compound able to control optionally a pot life after mixing other resin and a curing resin used the same as one component. However, an aliphatic polyamino compound with a low viscosity at a room temperature exhibits a small prolongation effect of a pot life.

Japanese Patent Kokai (Laid-open) No. 11-80322 relates to a compound obtainable by Michael addition reaction of a polyamino compound and an unsaturated carboxylic acid ester compound and discloses a method for prolongation of pot life in curing at a room temperature of an epoxy resin composition with a low viscosity at a room temperature and low harmfulness. However, when it is used as a curing agent for epoxy resin, the pot life of an epoxy resin composition used the curing agent becomes short since, during its long time preservation, ester-amide exchange reaction of an ester group and an amino group present in the amino compound proceeds, so that viscosity is increased due to production of amide and the ester group is decreased.

It has been already known that addition reaction of various amino compounds and an alkenyl compound produces the corresponding amino compound. When an alkenyl compound has a strong electron withdrawing group such as a cyano group or carboxylic acid ester, its reaction readily proceeds. On the other hand, when it has no strong electron withdrawing group, the reaction with the amino compound becomes difficult, but it becomes possible by use of a catalyst ("Progress of Complex Catalyst Chemistry" written by Shunichi Murahashi, Kagakuzokan 109, P167–176, 1986, published by Kagaku Dojin, in Japan). For example, acrylonitrile with a cyano group reacts readily with various amino compounds and a cyanoethylated amino compound thus obtained has been applied widely in the field of a curing agent for epoxy resin ("New Epoxy Resin" edited by Hiroshi Kakiuchi, published by Shokodo in Japan, P186, 1985). Further, reaction of acrylate or methacrylate having carboxylic acid ester with various amino compounds produces the corresponding amino compound (E.H. RIDDLE: MONOMERIC ACRYLIC ESTERS, P153–155, 1954)

Even in case of divinyl benzene where an alkenyl compound has no strong electron withdrawing group, it reacts N,N'-diethyl ethylenediamine by use of an alkaline metal catalyst whereby the corresponding amino compound is obtained (Japanese Patent Kokai (Laid-open) No. 55-11523). It has been known that a nitrogen-containing monomer with carbon-carbon double bond and amine is obtained by the reaction disclosed in Japanese Patent Kokai (Laid-open) No. 55-11523.

SUMMARY OF THE INVENTION

An object of the present invention is to provide an amino compound in which a long pot life is provided to an epoxy resin composition used the amino compound as a curing agent for epoxy resin and a process for producing the same.

As a result of extensive studies to provide above-mentioned novel amino compound in order to solve the above-mentioned prior art problems, the inventors have found that a novel amino compound is obtained by addition reaction of the diamine represented by the formula (1) and an alkenyl compound without necessitating use of a harmful raw material such as acrylonitrile designated as a specific chemical substance and a deleterious substance in Japan and the amino compound thus obtained causes no change of both viscosity during preservation and a pot life of an epoxy resin composition used the amino compound as a curing agent for epoxy resin and a long pot life is provided to an epoxy resin composition used the amino compound as a curing agent for epoxy resin, and have accomplished the present invention.

That is, the present invention provides an amino compound obtained by addition reaction of diamine represented by the following formula (1) and an alkenyl compound.

H₂N—H₂C—A—CH₂—NH₂          (1)

wherein A is a phenylene group or a cyclohexylene group.

The present invention provides also a process for producing an amino compound which comprises performing addition reaction of diamine represented by the formula (1) and an alkenyl compound in the presence of a strong base catalyst.

Further, the present invention provides a curing agent for epoxy resin containing the above-mentioned amino compound, an epoxy resin composition comprising an epoxy resin and the above-mentioned amino compound as a curing agent for epoxy resin and a cured product cured the epoxy resin composition.

DETAILED DESCRIPTION OF THE INVENTION

Figure 1:
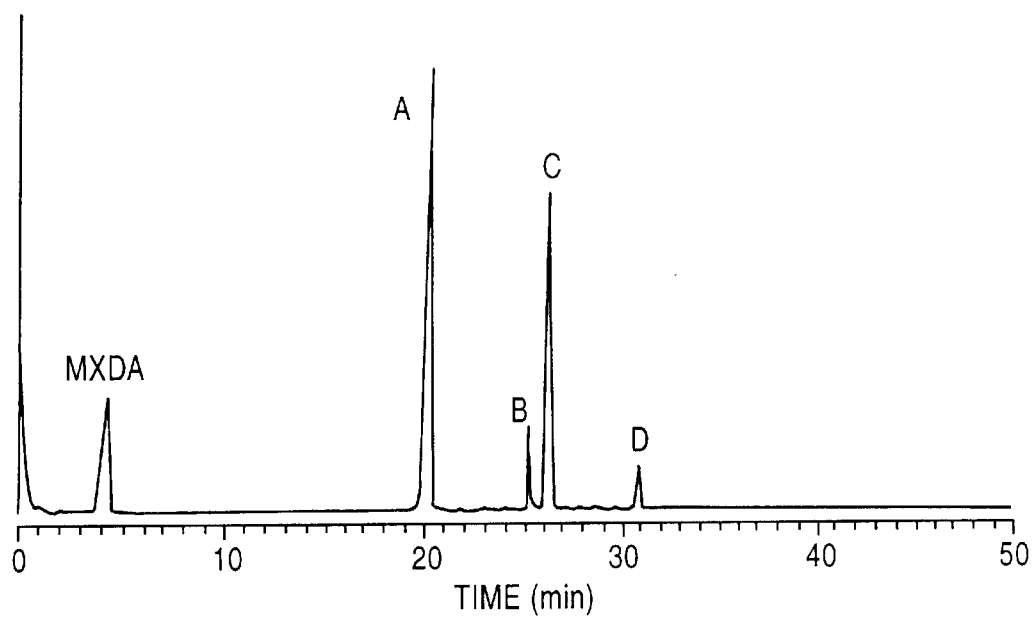
FIG. 1 is GC chromatgram of amino compound A synthesized in Example 1.

The present invention will be described in more detail below.

Examples of diamine represented by the formula (1) to be used in the present invention include orthoxylylenediamine, metaxylylenediamine, paraxylylenediamine, 1,2-bis(aminomethyl)cyclohexane, 1,3-bis(aminomethyl)cyclohexane and 1,4-bis(aminomethyl)cyclohexane, among which metaxylylenediamine and 1,3-bis(aminomethyl)cyclohexane are particularly preferable.

Further, diamine represented by the formula (1) mixed plural polyamino compounds can be used.

When an amount of other polyamino compound to be mixed is larger than an amount of diamine represented by the formula (1), it is preferable that the amount of other polyamino compound is 1 part by weight or below per 1 part by weight of damine represented by the formula (1) since the features to provide an epoxy resin cured coated film excellent in both gloss and levelling and to provide a cured product excellent in both water resistance and chemical resistance as features of diamine represented by the formula (1) cannot be maintained.

Examples of polyamino compound to be mixed with diamine represented by the formula (1) include aliphatic polyamines such as ethylenediamine, diethylenetriamine, triethylenetetramine, hexamethylenediamine and polyoxyalkylenepolyamine; alicyclic polyamines such as isophoronediamine, norbornanediamine, 1,4-diaminocyclohexane and di(aminohexyl)methane; aromatic polyamines such as metaphenylenediamine, diaminodiphenylmethane and diaminodiphenylsulfone and heterocyclic polyamines such as N-aminoethylpiperazine and 3,9-bis(3-aminopropyl) 2,4,8,10-tetraoxaspiro(5,5)undecane.

As the alkenyl compound to be used in the present invention, any alkenyl compounds can be applied. Examples of the alkenyl compound include ethylene, propylene, butene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene, styrene and divinylbenzene, among which styrene is particularly preferable.

The reaction proportion of alkenyl compound to diamine represented by the formula (1) is not limited on the condition that gelation is avoided. When the reaction proportion of alkenyl compound to diamine represented by the formula (1) is low, the amount of unreacted diamine is large. On the other hand, when the reaction proportion is high, the number of active hydrogen in an amino group becomes small. Therefore, in case of alkenyl compound with one carbon-carbon double bond, the reaction proportion is usually 0.1 to 4 mol of alkenyl compound and preferably 0.5 to 2 mol of alkenyl compound to 1 mol of diamine represented by the formula (1). In case of alkenyl compound with two carbon-carbon double bonds, the reaction proportion is usually 0.05 to 2 mol of alkenyl compound and preferably 0.25 to 1 mol of alkenyl compound to 1 mol of diamine represented by the formula (1). In case of using an alkenyl compound with one carbon-carbon double bond, when the reaction proportion is 1 mol of the alkenyl compound to 1 mol of diamine represented by the formula (1), an addition product in which 1 molecule of the alkenyl compound has been added to 1 molecule of diamine is obtained in the largest amount among obtained products and when the reaction proportion is 2 mol of alkenyl compound to 1 mol of diamine represented by the formula (1), an addition product in which 1 molecule of the alkenyl compound has been added to each of two primary amines in diamine is obtained in the largest amount among obtained products.

Examples of the catalyst to be used in the re present invention include any substance exhibiting strong basicity such as alkaline metal, alkaline metal amide and alkylated alkaline metal. Among them, alkaline metal amide by the general formula MNRR' wherein M is an alkaline metal; N is nitrogen and R and R' are, each independently, hydrogen or an alkyl group, is preferable and lithium amide (LiNH₂) is more preferable.

The amount of the catalyst depends on conditions such as species of raw material, reaction proportion and reaction temperature, and is usually 0.05 to 5% by weight and preferably 0.1 to 3% by weight. When the amount is below 0.05% by weight, the reaction rate becomes small, whereas above 5% by weight the reaction rate is not increased, so that it is not economical.

The reaction temperature is not limited on the condition that it is a melting point of diamine represented by the formula (1) or above, and is usually 25 to 150° C. and preferably 50 to 100° C. When the reaction temperature is below 25° C., the reaction rate of diamine represented by the formula (1) and an alkenyl compound is small, whereas above 150° C., it is desirable to select the reaction temperature depending on species of raw material, reaction proportion and species and amount of the catalyst since a polymer of the alkenyl compound is produced as a by-product.

The strong base catalyst such as alkaline metal amide readily reacts moisture or carbon dioxide in air. Therefore, it is necessary to exclude the influence of moisture and carbon dioxide by performing the reaction in an inert gas such as nitrogen, helium and argon.

In the reaction of the present invention, diamine represented by the formula (1), an alkenyl compound and alkaline metal amide as the catalyst are used. Since the reaction of diamine represented by the formula (1) and an alkenyl compound is an exothermic reaction, in order to maintain the reaction temperature to a constant temperature, it is necessary to control elevation of temperature to be caused due to exothermic reaction. Further, in order to depress the polymerization of alkenyl compound, it is preferable to add the alkenyl compound dropwise in the range of a constant reaction temperature. The time necessary to add the alkenyl compound dropwise is not limited. After the completion of the dropwise addition, it becomes possible to obtain intended compound by maintaining the reaction temperature to a constant temperature.

The reaction rate is greatly governed by species of amine and alkenyl compound, reaction proportion, reaction temperature and species and amount of catalyst. Thus, although the reaction time should be set depending on the above-mentioned conditions, it is preferable to sample the reaction liquid during the reaction and then determine the alkenyl compound as the raw material by gas chromatography or liquid chromatography and regard a time necessary to reach to 1% by weight or below of unreacted alkenyl compound as the reaction time.

After the completion of the reaction, the reaction liquid thus obtained comprises an amino compound and alkaline metal amide as the catalyst. The reaction liquid sometimes further contains unreacted diamine raw material and/or unreacted alkenyl compound. Regarding alkaline metal amide, it is possible to change alkaline metal amide to a readily removable salt thereof by adding acids such as hydrochloric acid, hydrogen chloride gas and acetic acid, alcohols such as methanol and ethanol or water and then filter it. For example, when water is used, alkaline metal amide is changed to hydroxide thereof, so that its filtration becomes easy.

The reaction liquid removed alkaline metal amide as the catalyst comprises an amino compound containing ① 1:1 addition reaction product wherein 1 molecule of alkenyl compound was added to 1 molecule of diamine, ② 1:2 addition product wherein 2 molecules of alkenyl compound were added to one primary amine in 1 molecule of diamine, ③ 1:2 addition product wherein each of 2 molecules of alkenyl compound was added to two primary amines in 1 molecule of diamine, ④ 1:3 addition product wherein 2 molecules of alkenyl compound were added to one primary amine in 1 molecule of diamine and 1 molecule of alkenyl compound was added to another primary amine in 1 molecule of diamine and ⑤ 1:4 addition product wherein 2 molecules (total 4 molecules) of alkenyl compound were added to each of two primary amines in 1 molecule of diamine. The reaction liquid sometimes further contains unreacted amine represented by the formula (1) and/or unreacted alkenyl compound. The contents of the addition products in the amino compound is governed by the reaction proportion of alkenyl compound to diamine represented by the formula (1). The higher the proportion of alkenyl compound, the proportion of addition product with a large number of addition molecule becomes larger.

The amino compound produced in the present invention is described in more detail below.

The amino compound of the present invention is an amino compound comprising a mixture of each addition compound with different side chain to each other represented by the following formula (2), obtained by addition reaction of diamine represented by the following formula (1) and an alkenyl compound.

wherein A is a phenylene group or a cyclohexylene group.

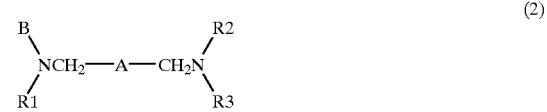

wherein A is as defined above; B is a derivative group of addition reacted alkenyl compound and R1, R2 and R3 are, each independently, hydrogen or a derivative group of addition reacted alkenyl compound.

When the above-mentioned alkenyl compound is styrene, the amino compound to be produced is represented by the following formula (3).

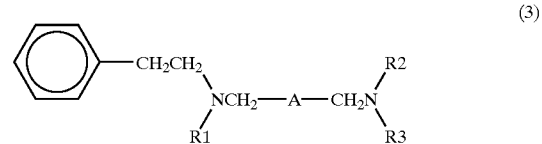

wherein A is as defined above and R1, R2 and R3 are, each independently, hydrogen or a phenethyl group.

The amino compound obtained in the present invention has reactivity with an epoxy resin or isocyanate and is useful as a curing agent for epoxy resin and a chain extender for polyurethane resin.

When the amino compound obtained by addition reaction of diamine represented by the formula (1) and an alkenyl compound is applied to a curing agent for epoxy resin, the curing agent for epoxy resin is used alone or as a mixture with a polyamino curing agent for epoxy resin in which the mixing ration is not limited.

When the amino compound obtained by addition reaction of diamine represented by the formula (1) and an alkenyl compound is applied to a curing agent for epoxy resin, modified amine also as a raw material of a polyamino curing agent for epoxy resin can be used. In this case, it is preferable to use an amino compound obtained by addition reaction in the reaction proportion of 0.1 to 1 mol to 1 mol of diamine represented by the formula (1). As a method for modification of amine, methods to be applied to conventional polyamino curing agent may be applied and is not limited. Further, the reaction proportion in the modification is not limited on the condition that gelling is avoided and a compound thus obtained has an amino group with active hydrogen.

PREFERRED EMBODIMENT OF THE INVENTION

The present invention will be described in more detail below, referring to Examples which are not intended to limit the scope of the present invention.

Analysis of amino compound and evaluation of pot life were performed by the following method.

Analysis of Amino Compound (1) Gas Chromatography Analysis
(hereinafter, "GC analysis",
column: trade name "Ultra Alloy-1" Frontier Laboratories Ltd., length 15 m, film thickness 1.5 μm, inner diameter 0.5 mm
column: 110° C./10 minutes+elevation of temperature temperature at the rate of 10° C./minute+300° C./60 minutes
(2) Nuclear Magnetic Resonance Absorption (NMR) Method
($^1$H-NMR, $^{13}$C-NMR)

JNM-AL400 type nuclear magnetic resonance absorption apparatus, manufactured by Japan Electron Optics Laboratory Co., in Japan was used.

δ (ppm) indicates a chemical shift represented by the following formula.

$$\delta \text{ (ppm)} = 10^6 \times (v_s - v_R)/v_R$$

$v_s$: resonance frequency (Hz) of a sample
$v_R$: resonance frequency (Hz) of trimethylsilane(TMS) as standard substance Evaluation of Pot Life 50 g of an epoxy resin composition was put in a polypropylene cup of 100 ml and standing under the conditions of 23° C. and 50%RH and time to peak exothermic temperature was measured.

The symbol "-" shows the result that generation of heat was not observed.

EXAMPLE 1

408.3 g (3.0 mol) of metaxylylenediamine, manufactured by Mitsubishi Gas Chemical Co., Inc., in Japan (hereinafter, "MXDA") and 22.3 g (0.97 mol) of lithium amide, a reagent manufactured by Merck KGaA, were charged to a one L (liter) vessel reactor, equipped with an agitator, a thermometer, a nitrogen gas inlet, a dropping funnel and a condenser and its interior temperature was raised to 80° C. in a nitrogen gas stream with stirring. After the elevation of temperature, 312.6 g (3.0 mol) of styrene, special grade reagent, manufactured by Wako Pure Chemical Industries, Ltd., in Japan was added thereto dropwise over 6 hours. After the dropwise addition, its interior temperature was maintained to 80° C. for one hour and then cooled to a room temperature and 17.5 g (0.97 mol) of water as amount of equal mol to charged lithium amide was added thereto and stirred. Then, filtration was performed to separate precipitates and then remained water was removed by vacuum distillation and filtration was again performed, whereby 654.9 g of amino compound A was obtained. The viscosity of amino compound A was 41 mPa·s/25° C. Unreacted styrene was 0.03% by weight (hereinafter, "wt %") and free MXDA was 15.1 wt %.

GC analysis of amino compound A thus obtained was performed. Four peaks other than peak of unreacted MXDA were detected. When the four peaks were assumed as peaks A, B, C and D in the order of retention time, the peak area ratio was MXDA; 15.8%, peak A; 49.3%, peak B; 3.0%, peak C; 28.7% and peak D:3.3% (refer to FIG. 1).

EXAMPLE 2

136.2 g (1.0 mol) of MXDA, and 10.7 g (0.47 mol) of lithium amide, were charged to a 500 mL vessel reactor, equipped with an agitator, a thermometer, a nitrogen gas inlet, a dropping funnel and a condenser and its interior temperature was raised to 80° C. in a nitrogen gas stream with stirring. After the elevation of temperature, 208.4 g (2.0 mol) of styrene was added thereto dropwise over 6 hours. After dropwise addition, its interior temperature was maintained to 80° C. for one hour and then cooled to a room temperature and then 8.5 g (0.47 mol) of water was added thereto and stirred. Then, filtration was performed to separate precipitates and then remained water was removed by vacuum distillation and filtration was again performed, whereby 255.8 g of amino compound B was obtained. The viscosity of amino compound B was 162 mPa·s/25° C. Unreacted styrene was 0.03 wt % and free MXDA was 0.62 wt %.

Figure 2:
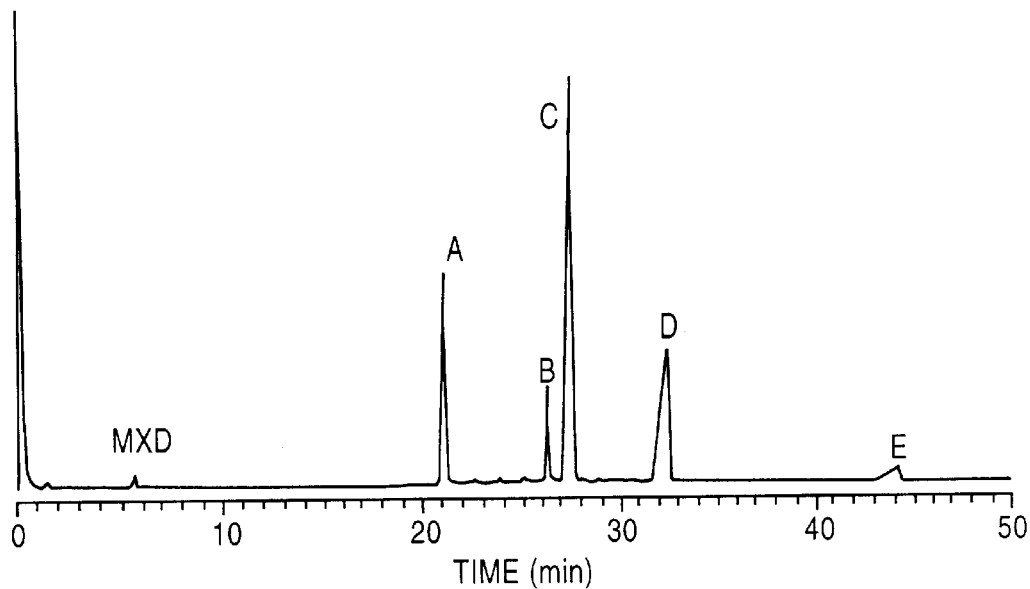
FIG. 2 is GC chromatgram of amino compound B synthesized in Example 2.

GC analysis of amino compound B thus obtained was performed. Peak E with longer retention time other than peaks A, B, C and D detected in GC analysis of the product obtained in Example 1 was detected. The peak area ratio was MXDA; 0.8%, peak A; 15.3%, peak B; 5.8%, peak C; 49.7%, peak D; 26.1% and peak E; 2.4% (refer to FIG. 2).

Figure 3:
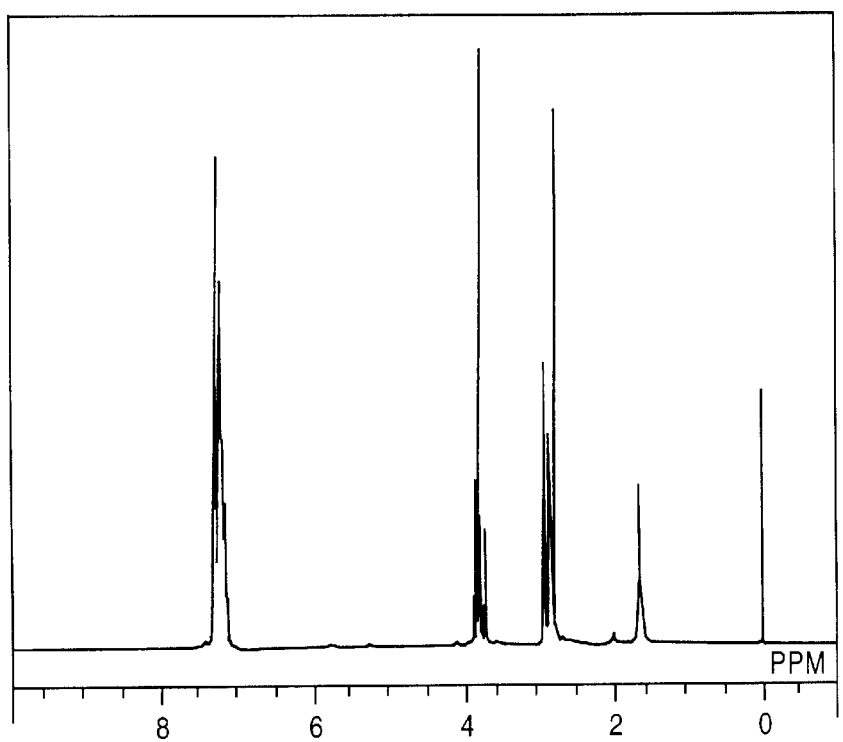
FIG. 3 is ¹H-NMR spectrum of amino compound B synthesized in Example 2.

$^1$H-NMR measurement was performed for amino compounds A and B produced in the addition reaction. $^1$H-NMR spectrum of amino compound B was shown in FIG. 3.

From results of $^1$H-NMR measurement, in amino compounds A and B, 1.42 ppm (1H, s, N$\underline{H}$, N$\underline{H}_2$), 2.76~2.91 (4H, m, Ar—C$\underline{H}_2$—CH$_2$—, —CH$_2$—C$\underline{H}_2$—NH—), 3.69~3.90 (4H, m, Ar—C$\underline{H}_2$—NH$_2$, Ar—C$\underline{H}_2$—NH—), 7.09~7.28 (9H, m, $\underline{\text{Ar}}$) were detected. Thus, it was confirmed that peaks A, B, C, D and E were products obtained by addition reaction of MXDA and styrene.

Figure 4:
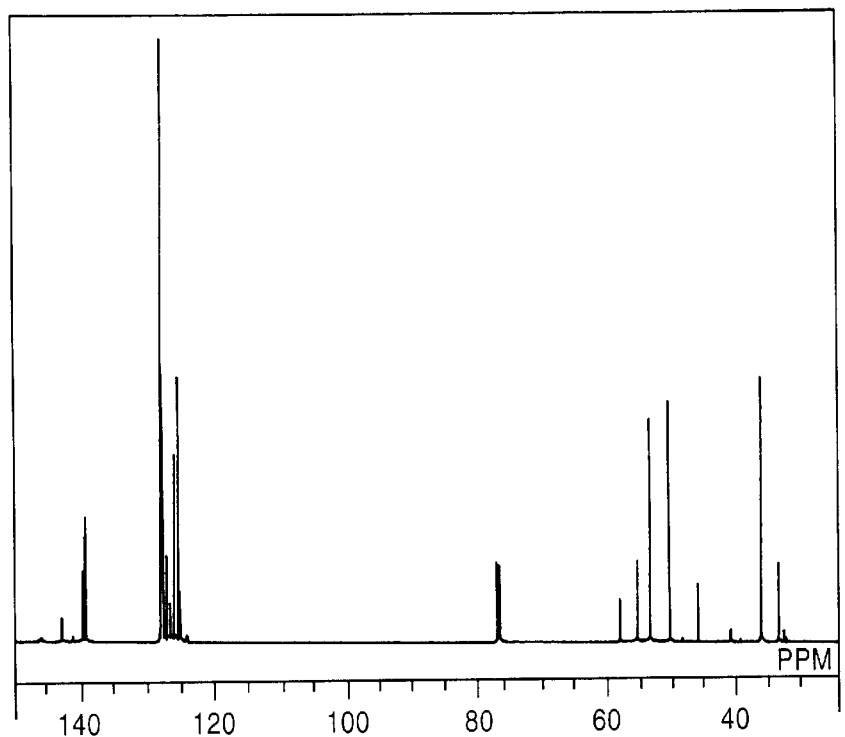
FIG. 4 is ¹³C-NMR spectrum of amino compound B synthesized in Example 2.

$^{13}$C-NMR measurement was performed for amino compounds A and B produced in the addition reaction. $^{13}$C-NMR spectrum of amino compound B was shown in FIG. 4.

From results of $^{13}$C-NMR measurement, each chemical species of peaks A, B, C, D and E was identified.

The spectrum derived from peak A was:

$^1$H-NMR δ [ppm]; 1.42 (1H, s, —N$\underline{H}$—, —N$\underline{H}_2$), 2.76~2.91 (4H, m, —NH—C$\underline{H}_2$—CH$_2$—, —CH$_2$—C$\underline{H}_2$—Ar), 3.69~3.90 (4H, m, H$_2$N—$\underline{H}_2$C—Ar, Ar—C$\underline{H}_2$—NH—), 7.12~7.28 (9H, m, $\underline{\text{Ar}}$), and $^{13}$C-NMR δ [ppm]; 36.2 (Ar—$\underline{C}$H$_2$—CH$_2$—NH—), 46.3 (Ar—$\underline{C}$H$_2$—NH$_2$—), 50.4 (—CH$_2$—$\underline{C}$H$_2$—NH—), 53.6 (—NH—$\underline{C}$H$_2$—Ar), 125.2 ($\underline{\text{Ar}}$), 125.7 ($\underline{\text{Ar}}$), 126.0 ($\underline{\text{Ar}}$), 126.3 ($\underline{\text{Ar}}$), 128.0 ($\underline{\text{Ar}}$), 128.1 ($\underline{\text{Ar}}$), 128.3 ($\underline{\text{Ar}}$), 139.8 ($\underline{\text{Ar}}$), 140.4 ($\underline{\text{Ar}}$), 143.2 ($\underline{\text{Ar}}$).

The spectrum derived from peak B was:

$^1$H-NMR δ [ppm]; 1.42 (1H, s, —N$\underline{H}$—, —N$\underline{H}_2$), 2.76~2.90 (4H, m, —NH—C$\underline{H}_2$—CH$_2$—, —CH$_2$—C$\underline{H}_2$—Ar), 3.69~3.87 (4H, m, H$_2$N—$\underline{H}_2$C—Ar, Ar—C$\underline{H}_2$—NH—), 7.09~7.28 (9H, m, $\underline{\text{Ar}}$), and $^{13}$C-NMR δ [ppm]; 33.5 (Ar—$\underline{C}$H$_2$—CH$_2$—N<), 46.3(Ar—$\underline{C}$H$_2$—NH$_2$), 55.4 (—CH$_2$—$\underline{C}$H$_2$—N<), 58.2 (Ar—$\underline{C}$H$_2$—N<), 125.5 ($\underline{\text{Ar}}$), 128.4 ($\underline{\text{Ar}}$), 139.8 ($\underline{\text{Ar}}$), 140.4 ($\underline{\text{Ar}}$), 143.0 ($\underline{\text{Ar}}$).

The spectrum derived from peak C was:

$^1$H-NMR δ [ppm]; 1.42 (1H, s, —N$\underline{H}$—, —N$\underline{H}_2$), 2.76~2.90 (4H, m, —NH—C$\underline{H}_2$—CH$_2$—, —CH$_2$—C$\underline{H}_2$—Ar), 3.69~3.87 (4H, m, H$_2$N—$\underline{H}_2$C—Ar, Ar—C$\underline{H}_2$—NH—), 7.09~7.28 (9H, m, $\underline{\text{Ar}}$), and $^{13}$C-NMR δ [ppm]; 36.2 (Ar—$\underline{C}$H$_2$—CH$_2$—NH—), 50.4 (—CH$_2$—$\underline{C}$H$_2$—NH—), 53.6 (—NH—$\underline{C}$H$_2$—Ar), 125.2 ($\underline{\text{Ar}}$), 125.5 ($\underline{\text{Ar}}$), 127.3 ($\underline{\text{Ar}}$), 127.8 ($\underline{\text{Ar}}$), 128.4 ($\underline{\text{Ar}}$), 139.8 ($\underline{\text{Ar}}$), 140.2 ($\underline{\text{Ar}}$).

The spectrum derived from peak D was:

$^1$H-NMR δ [ppm]; 1.42 (1H, s, —N$\underline{H}$—, —N$\underline{H}_2$), 2.76~2.90 (4H, m, Ar—C$\underline{H}_2$—CH$_2$—, —CH$_2$—C H₂—NH—), 3.69~3.87 (4H, m, Ar—CH₂—NH₂, Ar—C
H₂—NH—), 7.09~7.28 (9H, m, Ar), and ¹³C-NMR δ [ppm];
33.5 (Ar—CH₂—CH₂—N<), 36.2 (Ar—
CH₂—CH₂—NH—), 50.4 (—CH₂—CH₂—NH—), 53.6
(—NH—CH₂—Ar), 55.4 (—CH₂—CH₂—N<), 58.2 (Ar—
CH₂—N<), 125.5 (Ar), 125.7 (Ar), 126.1 (Ar), 126.8 (Ar),
127.8 (Ar), 128.0 (Ar), 128.3 (Ar), 128.4 (Ar), 139.6 (Ar),
139.8 (Ar), 140.0 (Ar), 140.4 (Ar).

The spectrum derived from peak E was:

¹H-NMR δ [ppm]; 1.42 (1H, s, —NH—, —NH₂),
2.76~2.91 (4H, m, Ar—CH₂—CH₂—, —CH₂—C
H₂—NH—), 3.69~3.90 (4H, m, Ar—CH₂—NH₂, Ar—C
H₂—NH—), 7.12~7.28 (9H, m, Ar), and ¹³C-NMR δ [ppm];
33.5 (Ar—CH₂—CH₂—N<), 55.4 (—CH₂—CH₂—N<),
58.2 (Ar—CH₂—N<), 125.5 (Ar), 128.4 (Ar), 139.2 (Ar),
140.4 (Ar).

The attribution results of peak by ¹³C-NMR was shown in Table 1.

It was confirmed that the amine compound produced by addition reaction was a mixture of primary amine, secondary amine and tertiary amine with different proportion to each other.

Peak A is an addition product represented by the formula (4) added 1 molecule of styrene to 1 molecule of MXDA in which 46.3 ppm (Ar—CH₂—NH₂) shows the presence of primary amine and 36.2 ppm (Ar—CH₂—CH₂—NH—), 50.4 ppm (—CH₂—CH₂—NH—) and 53.6 ppm (—NH—CH₂—Ar) show the presence of secondary amine.

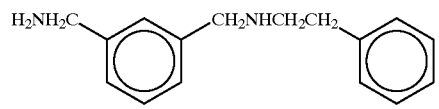

(4)

Likewise, peak B is an addition product represented by the formula (5) added 2 molecules of styrene to one of primary amines in MXDA in which 46.3 ppm (Ar—CH₂—NH₂—) shows the presence of primary amine and 33.5 ppm (Ar—CH₂—CH₂—N<), 55.4 ppm (—CH₂—CH₂—N<) and 58.2 ppm (Ar—CH₂—N<) show the presence of tertiary amine.

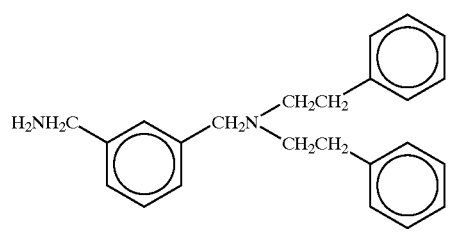

(5)

Likewise, peak C is an addition product represented by the formula (6) added 1 molecule of styrene to each of two primary amines in MXDA in which 36.2 ppm (Ar—CH₂—CH₂—NH—), 50.4 ppm (—CH₂—CH₂—NH—) and 53.6 ppm (—NH—CH₂—Ar) show the presence of secondary amine.

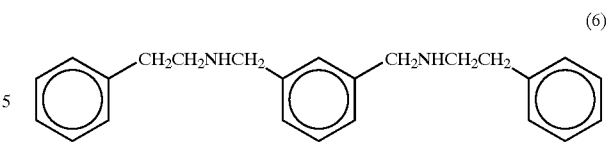

(6)

Likewise, peak D is an addition product represented by the formula (7) added 1 molecule of styrene to one of primary amines in MXDA and 2 molecules of styrene to another one of primary amines in MXDA in which 36.2 ppm (Ar—CH₂—CH₂—NH—), 50.4 ppm (—CH₂—CH₂—NH—) and 53.6 ppm (—NH—CH₂—Ar) show the presence of secondary amine and 33.5 ppm (Ar—CH₂—CH₂—N<), 55.4 ppm (—CH₂—CH₂—N<) and 58.2 ppm (Ar—CH₂—N<) show the presence of tertiary amine.

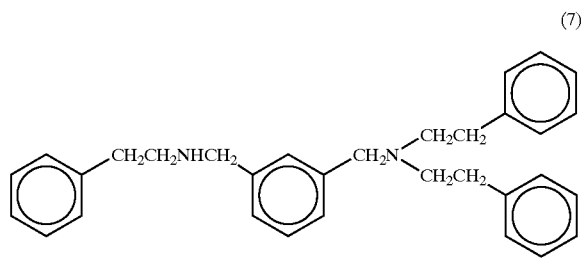

(7)

Likewise, peak E is an addition product represented by the formula (8) added 2 molecules of styrene to each of two primary amines in 1 molecule of MXDA in which 33.5 ppm (Ar—CH₂—CH₂—N<), 55.4 ppm (—CH₂—CH₂—N<) and 58.2 ppm (Ar—CH₂—N<) show the presence of tertiary amine.

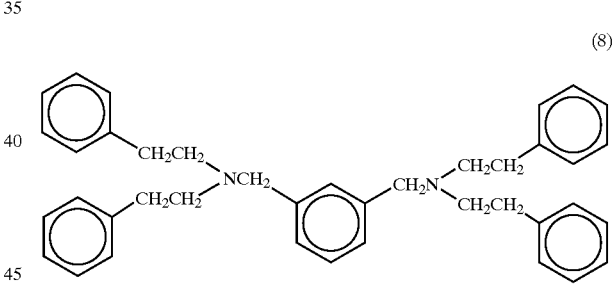

(8)

EXAMPLE 3

142.2 g (1.0 mol) of 1,3-bis(aminomethyl)cyclohexane, manufactured by Mitsubishi Gas Chemical Co., Inc., in Japan (hereinafter, "1,3-BAC") and 7.6 g (0.33 mol) of lithium amide were charged to a 500 mL vessel reactor, equipped with an agitator, a thermometer, a nitrogen gas inlet, a dropping funnel and a condenser and its interior temperature was raised to 80° C. in a nitrogen gas stream with stirring. After the elevation of temperature, 104.2 g (1.0 mol) of styrene was added thereto dropwise over 6 hours. After the dropwise addition, its interior temperature was maintained to 80° C. for one hour and then cooled to a room temperature and then 5.9 g (0.33 mol) of water was added thereto and stirred. Then, filtration was performed to separate precipitates and then remained water was removed by vacuum distillation and filtration was again performed, whereby 221.8 g of amino compound C was obtained. The viscosity of amino compound C was 45 mPa·s/25° C. Unreacted styrene was 0.03 wt % and free 1,3-BAC was 15.1 wt %.

EXAMPLE 4

142.2 g (1.0 mol) of 1,3-BAC and 10.9 g (0.47 mol) of lithium amide were charged to a 500 mL vessel reactor, equipped with an agitator, a thermometer, a nitrogen gas inlet, a dropping funnel and a condenser and its interior temperature was elevated up to 80° C. in a nitrogen gas stream with stirring. After the elevation of temperature, 208.4 g (2.0 mol) of styrene was added thereto dropwise over 6 hours. After the dropwise addition, its interior temperature was maintained to 80° C. for one hour and then cooled to a room temperature and then 8.5 g (0.47 mol) of water was added thereto and stirred. Then, filtration was performed to separate precipitates and then remained water was removed by vacuum distillation and filtration was again performed, whereby 315.5 g of amino compound D was obtained. The viscosity of amino compound D was 212 mPa·s/25° C. Unreacted styrene was 0.01 wt % and free 1,3-BAC was 0.83 wt %.

The chemical species contained in amino compounds C and D were identified in the same manner as in amino compounds A and B. It was confirmed that each was a product obtained by addition reaction of 1,3-BAC and styrene.

EXAMPLE 5

42 g of amino compound A as an addition product in a charge molar ratio of 1 mol of styrene to 1 mol of MXDA was added to 100 g of bisphenol A type liquid epoxy resin with an epoxy equivalent of 190, manufactured by Japan Epoxy Resins Co., Ltd., trade name; Epicoat 828 to mix, whereby an epoxy resin composition was prepared. Pot life of the epoxy resin composition thus obtained was evaluated. The evaluation result was shown in Table 2.

EXAMPLE 6

91 g of amino compound B as an addition product in a charge molar ratio of 2 mol of styrene to 1 mol of MXDA was added to 100 g of bisphenol A type liquid epoxy resin with an epoxy equivalent of 190, manufactured by Japan Epoxy Resins Co., Ltd., trade name; Epicoat 828 to mix, whereby an epoxy resin composition was prepared. Pot life of the epoxy resin composition thus obtained was evaluated. The evaluation result was shown in Table 2.

EXAMPLE 7

43 g of amino compound C as an addition product in a charge molar ratio of 1 mol of styrene to 1 mol of 1,3-BAC was added to 100 g of bisphenol A type liquid epoxy resin with an epoxy equivalent of 190, manufactured by Japan Epoxy Resins Co., Ltd., trade name; Epicoat 828 to mix, whereby an epoxy resin composition was prepared. Pot life of the epoxy resin composition thus obtained was evaluated. The evaluation result was shown in Table 2.

EXAMPLE 8

92 g of amino compound D as an addition product in a charge molar ratio of 2 mol of styrene to 1 mol of 1,3-BAC was added to 100 g of bisphenol A type liquid epoxy resin with an epoxy equivalent of 190, manufactured by Japan Epoxy Resins Co., Ltd., trade name; Epicoat 828 to mix, whereby an epoxy resin composition was prepared. Pot life of the epoxy resin composition thus obtained was evaluated. The evaluation result was shown in Table 2.

COMPARATIVE EXAMPLE 1

33 g of cyanoethylated metaxylylenediamine A as an addition product of 1 mol of acrylonitrile to 1 mol of MXDA was added to 100 g of bisphenol A type liquid epoxy resin with an epoxy equivalent of 190, manufactured by Japan Epoxy Resins Co., Ltd., trade name; Epicoat 828 to mix, whereby an epoxy resin composition was prepared. Pot life of the epoxy resin composition thus obtained was evaluated. The evaluation result was shown in Table 2.

COMPARATIVE EXAMPLE 2

65 g of cyanoethylated metaxylylenediamine B as an addition product of 2 mol of acrylonitrile to 1 mol of MXDA was added to 100 g of bisphenol A type liquid epoxy resin with an epoxy equivalent of 190, manufactured by Japan Epoxy Resins Co., Ltd., trade name; Epicoat 828 to mix, whereby an epoxy resin composition was prepared. Pot life of the epoxy resin composition thus obtained was evaluated. The evaluation result was shown in Table 2.

As clear from Examples, a novel amino compound was obtained by addition reaction of diamine represented by the formula (1) as a raw material and an alkenyl compound in the presence of a strong base catalyst. The amino compound thus obtained exhibits a prolongation effect in a pot life of an epoxy resin composition.

TABLE 1

| $\delta$ (ppm) | | Peak A | Peak B | Peak C | Peak D | Peak E |
|---|---|---|---|---|---|---|
| 33.5 | Ar—$\underline{C}H_2$—$CH_2$—N< | | ○ | | ○ | ○ |
| 36.2 | Ar—$\underline{C}H_2$—$CH_2$—NH— | ○ | | ○ | ○ | |
| 46.3 | Ar—$\underline{C}H_2$—$NH_2$ | ○ | ○ | | | |
| 50.4 | —$CH_2$—$\underline{C}H_2$—NH— | ○ | | ○ | ○ | |
| 53.6 | —NH—$\underline{C}H_2$—Ar | ○ | | | ○ | ○ |
| 55.4 | —$CH_2$—$\underline{C}H_2$—N< | | ○ | | ○ | ○ |
| 58.2 | Ar—$\underline{C}H_2$—N< | | ○ | | ○ | ○ |
| | primary amine | ○ | ○ | | | |
| | secondary amine | ○ | | ○ | ○ | |
| | tertiary amine | | ○ | | ○ | ○ |

TABLE 2

| Components of epoxy resin composition | Example 5 | Example 6 | Example 7 | Example 8 | Comp. Ex. 1 | Comp. Ex. 2 |
|---|---|---|---|---|---|---|
| Epicoat 828 (g) | 100 | 100 | 100 | 100 | 100 | 100 |
| amino compound A (g) | 42 | | | | | |
| amino compound B (g) | | 91 | | | | |
| amino compound C (g) | | | 43 | | | |
| amino compound D (g) | | | | 92 | | |
| cyanoethylated xylylenediamine A (g) | | | | | 33 | |
| cyanoethylated xylylenediamine B (g) | | | | | | 65 |
| Pot life | | | | | | |
| Time to peak exothermic temperature (min) | 348 | — | 220 | 635 | 287 | — |
| Peak exothermic temperature (° C.) | 40 | — | 66 | 28 | 31 | — |

What is claimed is:

1. An amino compound obtained by addition reaction of diamine represented by the following formula (1) and an alkenyl compound $$H_2N-H_2C-A-CH_2-NH_2 \quad (1)$$

wherein A is a phenylene group or a cyclohexylene group, and wherein said alkenyl compound is selected from the group consisting of ethylene, propylene, butene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene, styrene and divinylbenzene.

2. The amino compound comprising a mixture of each addition compound with different side chain to each other represented by the following formula (2), obtained by addition reaction of diamine represented by the following formula (1) and an alkenyl compound $$H_2N-H_2C-A-CH_2-NH_2 \quad (1)$$

wherein A is a phenylene group or a cyclohexylene group

wherein A is as defined above; B is a derivative group of addition reacted alkenyl compound and R1, R2 and R3 are, each independently, hydrogen or a derivative group of addition reacted alkenyl compound, wherein said alkenyl compound is selected from the group consisting of ethylene, propylene, butene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene, styrene and divinylbenzene.

3. The amino compound according to claim 2, comprising a mixture of each addition compound with different side chain to each other represented by the following formula (3), obtained by addition reaction of diamine represented by the formula (1) and styrene

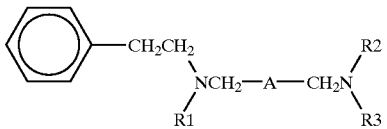

wherein A is as defined above and R1, R2 and R3 are, each independently, hydrogen or a phenethyl group.

4. The amino compound according to claim 2, further containing unreacted diamine represented by the formula (1) and/or unreacted alkenyl compound.

5. A process for producing an amino compound which comprises performing addition reaction of diamine represented by the following formula (1) and an alkenyl compound in the presence of a strong base catalyst $$H_2N-H_2C-A-CH_2-NH_2 \quad (1)$$

wherein A is a phenylene group or a cyclohexylene group.

6. The process for producing an amino compound according to claim 5, wherein said strong base catalyst is an alkaline metal amide catalyst by the general formula MNRR' in which M is an alkaline metal; N is nitrogen, and R and R' are, each independently, hydrogen or an alkyl group.

7. A curing agent for epoxy resin containing the amino compound described in claim 1.

8. An epoxy resin composition comprising an epoxy resin and the amino compound described in claim 1 as a curing agent for epoxy resin.

9. A cured product cured the epoxy resin composition described in claim 8.

10. A process according to claim 5, wherein said alkenyl compound is selected from the group consisting of ethylene, propylene, butene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene, styrene and divinylbenzene.

* * * * *